United States Patent [19]

Tesmann et al.

[11] Patent Number: 4,992,263

[45] Date of Patent: Feb. 12, 1991

[54] THICKENDED AQUEOUS SURFACTANT SOLUTIONS AND THEIR USE IN COSMETIC PREPARATIONS

[75] Inventors: Holger Tesmann, Duesseldorf; Hermann Hensen, Haan; Wolfgang Hochschon, Hilden; Uwe Ploog, Haan, all of Fed. Rep. of Germany

[73] Assignee: Henkel Kommanditgesellschaft auf Aktien, Duesseldorf-Holthausen, Fed. Rep. of Germany

[21] Appl. No.: 242,385

[22] Filed: Sep. 9, 1988

[30] Foreign Application Priority Data

Sep. 9, 1987 [DE] Fed. Rep. of Germany ....... 3730179

[51] Int. Cl.$^5$ ..................... A61K 7/021; A61K 7/025; A61K 7/07; A61K 7/09
[52] U.S. Cl. ......................................... 424/63; 424/64; 424/70; 424/71; 424/73; 424/74; 424/195.1; 424/677; 424/680; 514/2; 514/844; 514/845; 514/846; 514/847; 514/848; 514/941; 252/173; 252/174.11; 252/174.22
[58] Field of Search .................. 424/677, 680, 70, 71, 424/73, 74, 63, 64, 195.1; 514/2, 844, 845, 846, 847, 848, 941; 252/174.22, 174.11, 173; 8/405

[56] References Cited

U.S. PATENT DOCUMENTS

| | | | |
|---|---|---|---|
| 4,123,378 | 10/1978 | Abel et al. | 252/174.16 |
| 4,184,978 | 1/1980 | France et al. | 514/785 X |
| 4,234,444 | 11/1980 | Wegener et al. | 252/174.22 |
| 4,288,339 | 9/1981 | Wilsberg | 252/174.22 X |
| 4,495,092 | 1/1985 | Schmid et al. | 252/559 |
| 4,551,330 | 11/1985 | Wagman et al. | 424/73 X |
| 4,608,189 | 8/1986 | Koch et al. | 252/174.22 |
| 4,719,104 | 1/1988 | Patel | 424/59 X |
| 4,777,037 | 10/1988 | Wagman et al. | 424/71 X |
| 4,824,602 | 4/1989 | Juneja | 424/70 |

FOREIGN PATENT DOCUMENTS

| | | |
|---|---|---|
| 755092 | 1/1971 | Belgium . |
| 14980 | 9/1980 | European Pat. Off. ....... 252/174.22 |
| 104434 | 4/1984 | European Pat. Off. . |
| 116905 | 8/1984 | European Pat. Off. . |
| 217250 | 8/1987 | European Pat. Off. . |
| 1628651 | 7/1971 | Fed. Rep. of Germany . |
| 2360107 | 12/1975 | Fed. Rep. of Germany . |
| 2283667 | 2/1976 | France . |
| 2324718 | 4/1977 | France . |
| 1238897 | 10/1986 | Japan ............................ 252/174.22 |

OTHER PUBLICATIONS

*McCutcheon's Emulsifiers & Detergents*, 1982, North American Edition, pp. 295, 297.
*CTFA Cosmetic Ingredient Dictionary*, 1973, First Edition, pp. 34–35, 117, 144, 172–173.
*The Merck Index*, Tenth Edition, pp. 1090, 1094, 1983.

*Primary Examiner*—John W. Rollins
*Attorney, Agent, or Firm*—Ernest G. Szoke; Wayne C. Jaeschke; Real J. Grandmaison

[57] ABSTRACT

Nitrogen-free thickeners in aqueous surfactant solutions comprising polyethoxylates of mono- and/or polyunsaturated $C_{12}$–$C_{22}$ fatty alcohols having an average degree of ethoxylation of 2 to 5, which also contain 1 to 2 terminal propylene oxide groups attached by condensation instead of the corresponding number of ethylene oxide groups. The products may also be used in admixture with dissolved inorganic electroltye salts and with polyethoxylates of saturated fatty alcohols. These surfactant solutions are useful in the formulation of personal hygiene preparations such as hair shampoos, foam baths, shower baths, handwashing pastes and the like.

27 Claims, No Drawings

THICKENDED AQUEOUS SURFACTANT SOLUTIONS AND THEIR USE IN COSMETIC PREPARATIONS

BACKGROUND OF THE INVENTION

1. Field of the Invention

This invention relates to thickened aqueous surfactant solutions as well as the use of such solutions in cosmetic preparations of the type used in the field of personal hygiene such as hair shampoos, foam baths, shower baths, handwashing pastes and the like.

2. Statement of the Related Art

Surfactant solution mixtures generally are formulated to contain anionic surfactants, such as alkyl ether sulfates, as the principal surfactant component. Thickeners are normally added to such solutions to stabilize the clear or disperse systems and to improve the handling properties. Many compounds are known as agents for increasing the viscosity of formulations containing anionic surfactants. The most simple and inexpensive means for regulating the viscosity of solutions containing anionic surfactants is to add sodium chloride or other inorganic water-soluble electrolyte salts. In addition to or instead of these inorganic components, it is also known to add soluble organic compounds having a thickening effect. Thus, it is known that fatty acid alkanolamides, such as coconut oil fatty acid monoethanolamide, lauric acid monoethanolamide, oleic acid diethanolamide and coconut oil fatty acid diethanolamide, have a thickening effect on many surfactant systems and increase the foam stability of the systems in the presence of fats. In addition, it is known that polyethylene glycol difatty acid esters and many water soluble polymers also have a thickening effect on aqueous surfactant solutions.

However, many thickeners such as recited above are attended by numerous disadvantages. Solutions thickened with polyethylene glycol fatty acid diester often show inadequate viscosity stability during storage and water-soluble polymers are often difficult to dissolve and may give rise to unwanted, slimy flow behavior with a tendency towards "stringing", which is highly undesirable in cosmetic preparations. Derivatives of diethanolamine such as fatty acid alkanolamides are increasingly undesirable in cosmetic preparations because they often contain a small content of free alkanolamine as a byproduct or impurity, which can give rise to the formation of nitrosamines.

DESCRIPTION OF THE INVENTION

Other than in the operating examples, or where otherwise indicated, all numbers expressing quantities of ingredients or reaction conditions used herein are to be understood as modified in all instances by the term "about".

The present invention provides new thickeners for aqueous surfactant preparations which do not have the disadvantages referred to above and which are not derivatives of amines or alkanolamines.

It has been found that the viscosity of aqueous compositions, particularly those containing one or more ionic surfactants, can be effectively increased by incorporating into the composition selected polyethoxylates of mono- and/or polyunsaturated fatty alcohols. The thickening effect of the preferred unsaturated fatty alcohol polyethoxylates in accordance with this invention clearly exceeds the corresponding effect of thickeners commonly used in the art.

The aqueous surfactant solution compositions of this invention contain one or more nitrogen-free thickeners comprising polyethoxylates of mono- and/or polyunsaturated $C_{12}$–$C_{22}$ fatty alcohols having an average degree of ethoxylation of approximately 2 to 5. The compositions may also contain dissolved inorganic electrolyte salts which have a thickening effect. The polyethoxylates may be further characterized as containing one or at most two terminal propylene oxide groups attached by means of a condensation reaction as a substitute for the corresponding number of ethylene oxide groups.

Unsaturated alcohol polyethoxylates having an average degree of ethoxylation of from 2.5 to 4.5 and more preferably from 3 to 4 are particularly suitable. Optimal thickening effects are obtained within this range and more particularly at values of 3.5.

In a preferred embodiment of the invention, the aqueous surfactant solution compositions of this invention may also contain one or more polyethoxylates of saturated fatty alcohols in addition to or admixture with the polyethoxylates of the mono- and/or polyunsaturated fatty alcohols referred to above. Preferably these saturated polyethoxylates have approximately the same chain length and approximately the same degree of polyethoxylation as the unsaturated polyethoxylates referred to above.

Preferred fatty alcohol polyethoxylate mixtures contain predominantly $C_{16}$–$C_{20}$ and more preferably $C_{16}$–$C_{18}$ chain length components. As in the case of the unsaturated polyethoxylates, the saturated polyethoxylates may also contain one or two propylene oxide groups attached by condensation as a substitute for a corresponding number of ethylene oxide groups.

Fatty alcohol ethoxylates based on unsaturated $C_{16}$–$C_{22}$ fatty alcohols having iodine values of 45 to 170 and a degree of ethoxylation of about 2 to 5 alone or admixed with saturated $C_{12}$–$C_{18}$ fatty alcohol ethoxylates having a degree of ethoxylation of from about 2 to 5 are particularly preferred thickener substances for the purposes of this invention.

The unsaturated fatty alcohol polyethoxylates normally contain 1 to 3 ethylenic double bonds in the unsaturated fatty alcohol radicals. The monoethylenically unsaturated components generally represent the main component, particularly where starting materials of natural origin are used.

In the preferred embodiment of the invention, the aqueous surfactant solution composition of the invention contains a mixture of the aforementioned saturated and unsaturated fatty alcohol polyethoxylates wherein at least 50% by weight of such mixture, and preferably about 55 to 90% by weight of such mixture, is composed of the unsaturated fatty alcohol polyethoxylates. Unsaturated fatty alcohols and mixtures thereof with saturated fatty alcohols may be obtained in known manner from fats, fatty acid esters or fatty acids of natural origin.

Carboxylic acid groups may be converted to alcohol groups by a reduction reaction in the presence of a catalyst which will cause little, if any, hydrogenation of the ethylenic double bonds present in the carbon chains. Suitable fatty alcohol mixtures of natural origin having a considerable content of unsaturated components are, for example, the products marketed by Applicants under the trade names "HD-Ocenol 50/55" and "HD- Ocenol 80/85", which have substantially the following composition:

| Carbon Chain Length | HD-Ocenol 50/55 % by weight specification | Typical Content % by weight | HD-Ocenol 80/85 % by weight specification | Typical Content % by weight |
|---|---|---|---|---|
| C 12 | 0-2 | (approx. 1) | 0-2 | (approx. 1) |
| C 14 | 2-7 | (approx. 5) | 2-7 | (approx. 5) |
| C 16 | 25-35 | (approx. 30) | 8-18 | (approx. 13) |
| C 18 |  | (approx. 20) |  |  |
| C 18' | 55-75 | (approx. 41) | 70-83 | (approx. 71) |
| C 18" |  | (approx. 1) |  | (approx. 4) |
| C 18'" |  | (approx. 1) |  | (aprox. 2) |
| C 20 | 0-2 | (approx. 1) | 0-3 | (approx. 2) |

The carbon chain distribution of another thickener based on an unsaturated fatty alcohol obtained from rapseed oil and sold under the Trade Name "Rubocenol" corresponds substantially to the following composition:

| Carbon Chain Length | Typical Content % by weight |
|---|---|
| C 16 | approx. 7.0 |
| C 16' | approx. 2.0 (palmitoleyl alcohol) |
| C 18 | approx. 3.0 |
| C 18' | approx. 70.0 (oleyl alcohol) |
| C 18" | approx. 8.0 (linoleyl alcohol). |
| C 18'" | approx. 7.0 (linolenyl alcohol) |
| C 20 | approx. 3.0 |

In the above lists, the particular number of ethylenic double bonds present is indicated by the number of apostrophies.

The aqueous surfactant solution compositions of this invention are formulated for use in cosmetic preparations containing one or more ionic surfactants which preparations may also contain one or more water soluble inorganic electrolyte salts as adjunct thickening agents. Preferably, such preparations contain 5 to 20% by weight of ionic surfactant, 1 to 5% by weight of the nitrogen-free water soluble thickener described above, and optionally up to 10% by weight of the water-soluble inorganic electrolyte salt. Where such electrolyte salt is present, it is generally present at a minimum level of 0.5% by weight, with the preferred range being 1.0 to 3.5% by weight. The preparations may also contain minor quantities of other known standard additives for cosmetic preparations, the balance of the formulation being water.

The water-soluble ionic surfactants may comprise anionic, zwitterionic and cationic surfactants. Preferred ionic surfactants are distinguished by a lipophilic, preferably linear $C_8$-$C_{18}$ alkyl or alkenyl group which preferably has attached terminally thereto an anionic group which disassociates in water. Such anionic groups include sulfate (—$OSO_3^-$), sulfonate (—$SO_3^-$), phosphate (—O—$PO_3^{--}$) or carboxylate (—$COO^-$). The cationic group may include a quaternary ammonium group such as —$N^+(CH_3)_3$.

The zwitterionic groups include —$N^+(CH_3)_2$—$CH_2$—$COO^-$ or

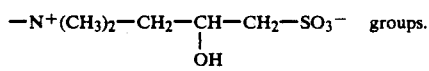 groups.

Preferred anionic surfactants include alkylsulfates, alkylpolyglycol ether sulfates, alkanesulfonates, sulfosuccinic acid monoalkyl esters and monopolyethoxyalkyl esters, monoalkylphosphates, protein fatty acid condensates, acyl isethionates, acyl taurides, soaps and acyl sarcosides. Preferred cationic surfactants include alkyl trimethyl ammonium halides, alkyldimethyl benzylammonium halides, alkylpyridinium halides, and alkylimidazolinium halides. Suitable zwitterionic surfactants include N-alkyl-N,N-dimethyl glycine and N-acylamino-propyl-N,N-dimethyl glycine. Mixtures of the above mentioned ionic surfactants or mixtures of anionic or cationic and zwitterionic surfactants may also be used as the ionic surfactant component of the composition.

It is particularly desirable for the purposes of this invention to provide compositions and preparations having high viscosity on the one hand and a comparatively low content of ionic surfactant on the other hand. In this case it is found that such compositions containing a combination of the thickeners of the present invention and an inorganic electrolyte salt give rise to a synergistic improvement in the thickening properties of aqueous solutions in which they are present.

Inorganic electrolyte salts which may be used include water-soluble alkali metal, ammonium and alkaline earth metal salts, such as fluorides, chlorides, bromides, sulfates, phosphates, and nitrates. The chlorides or sulfates of an alkali metal, ammonium or magnesium are preferred. Sodium chloride and magnesium chloride are particularly preferred. In addition, the aqueous preparations according to the invention may optionally contain other components which render them more suitable for the particular application envisaged. For example, they may contain nonionic surfactants, preferably in relatively small quantities of from 5 to 50% by weight of the ionic surfactants present. Finally, they may contain small quantities of perfumes, dyes, opacifiers and pearlescers, antimicrobial agents, preservatives, skin-cosmetic components, vegetable extracts, protein hydrolyzates, buffers, complexing agents and other known auxiliaries and additives of the type normally used in shampoos, bath additives, shower bath preparations, liquid soaps, liquid skin-cleansing preparations, liquid hair shampoos, and also in liquid laundry and dishwashing detergents and liquid domestic cleaning preparations based on ionic surfactants.

EXAMPLES 1-16

In the following examples, various aqueous formulations were prepared containing different combinations of ionic surfactant, polyethoxylate thickeners and sodium chloride as the electrolyte salt component, the balance being water. In all cases, these formulations contained 10% by weight of the ionic surfactant and 3% by weight of the polyethoxylate thickener identified in Tables 1 and 2. To these formulations was added X% by weight of NaCl which is identified in the Tables as the amount of NaCl in percent by weight required to achieve a viscosity of 4000 mPa.s. (1 Pascal second -Pa.s - approximates 1 centipoise second -cps -.)

The comparative thickening effect achieved by the combination of thickeners was then determined by increasing the amount of NaCl (X%) by 0.5% by weight. Comparative results are shown in Tables.

The maximum achievable viscosity and the total amount of NaCl required to achieve this viscosity are also reported in the Tables.

TABLE 1

| Example Number | Product containing "TEXAPON"NSO ionic surfactant AND; | X % NaCl for 4000 mPa.s | Viscosity (mPa.s) at X + 0.5% NaCl | Maximum Viscosity mPa.s | % NaCl |
|---|---|---|---|---|---|
| 1 | Comperlan KD | 1.5 | 16 000 | 30 000 | 3.5 |
| 2 | HD-Ocenol 50/55 + 2 EO | 1.5 | 38 000 | 38 000 | 2.0 |
| 3 | HD-Ocenol 50/55 + 3 EO | 2.0 | 36 000 | 37 000 | 3.0 |
| 4 | HD-Ocenol 50/55 + 4 EO | 2.5 | 21 000 | 33 000 | 3.5 |
| 5 | HD-Ocenol 50/55 + 5 EO | 2.5 | 12 000 | 20 000 | 4.0 |
| 6 | HD-Ocenol 80/85 + 2 EO | 1.0 | 10 000 | 10 000 | 1.5 |
| 7 | HD-Ocenol 80/85 + 3 EO | 2.0 | 39 000 | 39 000 | 2.5 |
| 8 | HD-Ocenol 80/85 + 4 EO | 2.0 | 11 000 | 32 000 | 3.5 |
| 9 | HD-Ocenol 80/85 + 5 EO | 2.5 | 10 000 | 19 000 | 4.0 |
| 10 | Rubocenol dist. + 3 EO | 2.0 | 38 000 | 38 000 | 2.5 |
| 11 | HD-Ocenol 50/55 + 2 EO + 1 PO | 1.5 | 18 000 | 36 000 | 2.5 |
| 12 | HD-Ocenol 50/55 + 3 EO + 1 PO | 3.0 | 9 000 | 12 000 | 4.5 |

TABLE 2

| Example Number | Product containing "TEXAPON" ionic surfactant AND; | X % NaCl for 4000 mPa.s | Viscosity (mPa.s) at X + 0.5% NaCl | Maximum Viscosity mPa.s | % NaCl |
|---|---|---|---|---|---|
| 13 | Comperlan KD | 2.5 | 6 500 | 8 000 | 4 |
| 14 | HD-Ocenol 50/55 + 3 EO | 2.0 | 9 000 | 15 000 | 3 |
| 15 | HD-Ocenol 50/55 + 4 EO | 4.0 | 9 000 | 21 000 | 5.5 |
| 16 | HD-Ocenol 50/55 + 5 EO | 5.5 | 7 000 | 9 000 | 7.0 |

Viscosity values were determined using a Hoeppler falling ball viscosimeter at 20° C. and are expressed in mPa.s.

The product designated by the trade name "Texapon NSO" in Table 1 is marketed by the Henkel Corporation of West Germany and is a fatty alcohol mixture having 12 to 14 carbon atoms (70 to 30 ratio) polyglycol ether - 2 EO sulfate, sodium salt, as a 28% by weight solution in water. The product designated by the trade name "Texapon ASV" in Table 2 is also marketed by Henkel Corporation and is a 30% aqueous solution of a magnesium salt of an alkyl ether sulfate based on a mixture of adducts of 2 to 10 mol ethylene oxide with a fatty alcohol mixture having 12 to 18 carbon atoms. The thickener product designated by the trade name "Comperlan KD" in Tables 1 and 2 is a coconut oil fatty acid diethanolamide also marketed by Henkel.

It is to be understood that the above described embodiments of the invention are illustrative only and that modifications throughout may occur to those skilled in the art.

We claim:

1. A thickened aqueous surfactant composition consisting essentially of a mixture of:
   (a) water,
   (b) from about 5 to 20% by weight of at least one water-soluble ionic surfactant.
   (c) from about 1 to about 5% by weight of a nitrogen-free thickener consisting essentially of polyethoxylates of unsaturated fatty alcohols having from about 12 to about 22 carbon atoms and having an average degree of ethoxylation of about 2 to about 5, and
   (d) from about 0.5 to about 10% by weight of a water-soluble inorganic electrolyte salt.

2. The composition of claim 1 wherein said unsaturated polyethoxylate contains at least one terminal propylene oxide group condensed therewith as a substitute for a corresponding number of ethylene oxide groups.

3. The composition of claim 2 wherein said unsaturated polyethoxylate contains two terminal propylene oxide groups condensed therewith.

4. The composition of claim 1 wherein said unsaturated polyethoxylate is based on fatty alcohols having predominantly about 16 to about 20 carbon atoms.

5. The composition of claim 4 wherein said unsaturated fatty alcohol polyethoxylates are mixtures containing from one to three ethylenic double bonds in the molecule.

6. The composition of claim 1 wherein said unsaturated polyethoxylates have an average degree of ethoxylation of about 2 to 4.5

7. The composition of claim 6 wherein said unsaturated polyethoxylates have an average degree of ethoxylation of about 3 to 4.

8. The composition of claim 1 wherein said nitrogen-free thickener consists essentially of a mixture of said unsaturated polyethoxylates and polyethoxylates of saturated fatty alcohols having from about 12 to about 22 carbon atoms.

9. The composition of claim 8 wherein said mixture of unsaturated and saturated polyethoxylates is present at a level of from about 1 to about 5% by weight and contains at least 50% by weight of said unsaturated polyethoxylates.

10. The composition of claim 9 wherein said mixture of unsaturated and saturated polyethoxylates contains from about 55 to about 90% by weight of said unsaturated polyethoxylates.

11. The composition of claim 9 wherein said saturated polyethoxylates are based on saturated fatty alcohols having predominantly from about 16 to about 20 carbon atoms.

12. The composition of claim 1 wherein said electrolyte salt is present at a level of from about 1 to about 3.5% by weight.

13. The composition of claim 1 wherein said electrolyte salt is selected from the group consisting of alkali metal, ammonium and alkaline earth metal salts.

14. The composition of claim 1 wherein said electrolyte salt is sodium chloride.

15. The composition of claim 1 wherein said nitrogen-free thickener consists essentially of a mixture of at least 50% by weight of polyethoxylates of unsaturated fatty alcohols having predominantly about 16 to about 20 carbon atoms and a degree of unsaturation of from 1 to 3 ethylenic double bonds and less than 50% by weight of polyethoxylates of saturated fatty alcohols having predominantly about 16 to about 20 carbon atoms.

16. The composition of claim 15 wherein said saturated and unsaturated polyethoxylates are based on fatty alcohols containing predominantly from about 16 to about 18 carbon atoms.

17. The composition of claim 16 wherein said fatty alcohols are of natural origin.

18. The composition of claim 16 wherein said of from about 3 to 4.

19. The composition of claim 16 wherein said electrolyte salt is present at a level of from about 1 to about 3.5% by weight.

20. The composition of claim 1 wherein said ionic surfactant is selected from the group consisting of anionic, zwitterionic and cationic surfactants, and mixtures thereof.

21. A thickened aqueous cosmetic preparation consisting essentially of a mixture of:
    (a) water,
    (b) from about 5 to about 20% by weight of at least one water-soluble ionic surfactant,
    (c) from about 1 to about 5% by weight of a nitrogen-free thickener consisting essentially of a mixture of at least about 50% by weight of polyethoxylates of unsaturated fatty alcohols having predominantly about 16 to about 20 carbon atoms, a degree of unsaturated of from 1 to 3 ethylenic double bonds and an average degree of polyethoxylation of from about 2 to about 5, mixed with less than 50% by weight of polyethoxylates of saturated fatty alcohols having predominantly about 16 to about 20 carbon atoms and an average degree of ethoxylation of from about 2 to about 5, and
    (d) from about 0.5 to about 10% by weight of a water-soluble electrolyte salt.

22. The preparation of claim 21 wherein said unsaturated and saturated polyethoxylates are based on fatty alcohols having predominantly about 16 to about 18 carbon atoms.

23. The preparation of claim 22 wherein said unsaturated polyethoxylate has one or two terminal propylene oxide groups condensed therewith as a substitute for a corresponding number of ethylene oxide groups.

24. The preparation of claim 22 wherein said unsaturated and saturated polyethoxylates have a degree of ethoxylation of from about 3 to 4.

25. The preparation of claim 24 wherein said water-soluble electrolyte salt is present at a level of from about 1 to about 3.5% by weight.

26. The preparation of claim 25 wherein said salt is sodium chloride.

27. The preparation of claim 21 further containing minor amounts of one or more cosmetic additives selected from the group consisting of perfumes, dyes, opacifiers, pearlescers, antimicrobial agents, preservatives, skin-cosmetic components, vegetable extracts, protein hydrolyzates, buffers and complexing agents.

* * * * *

UNITED STATES PATENT AND TRADEMARK OFFICE
CERTIFICATE OF CORRECTION

PATENT NO. : 4,992,263

DATED : February 12, 1991

INVENTOR(S) : Tesmann et al.

It is certified that error appears in the above-identified patent and that said Letters Patent is hereby corrected as shown below:

ON TITLE PAGE and Column 1;
In the title, "thickended" should read --THICKENED--.

In the claims, at claim 18, column 7, line 28 and 29, delete " of from about 3 to 4" and add --polyethoxylates have an average degree of ethoxylation of from about 3 to 4.--.

At claim 21, column 8, line 8, "unsaturated" should read --unsaturation--.

Signed and Sealed this

Twenty-first Day of July, 1992

*Attest:*

DOUGLAS B. COMER

*Attesting Officer*  Acting Commissioner of Patents and Trademarks